(12) United States Patent
Solem

(10) Patent No.: US 6,248,119 B1
(45) Date of Patent: Jun. 19, 2001

(54) DEVICE AND METHOD FOR ENDOSCOPIC VASCULAR SURGERY

(76) Inventor: Jan Otto Solem, Nordmannavägen 20, 237, 31, Bjärred (SE)

(*) Notice: Subject to any disclaimer, the term of this patent is extended or adjusted under 35 U.S.C. 154(b) by 0 days.

(21) Appl. No.: 09/599,453

(22) Filed: Jun. 22, 2000

(30) Foreign Application Priority Data

Feb. 28, 2000 (SE) .................................. 0000642

(51) Int. Cl.⁷ .................................. A61B 17/32
(52) U.S. Cl. .................................. 606/167; 606/185
(58) Field of Search .................................. 606/167, 184, 606/185, 159, 174

(56) References Cited

U.S. PATENT DOCUMENTS

| | | | |
|---|---|---|---|
| 5,595,193 | * | 1/1997 | Walus et al. .................. 606/167 |
| 5,725,544 | * | 3/1998 | Rygaard .................. 606/167 |
| 5,766,220 | | 6/1998 | Moenning . |
| 5,893,369 | | 4/1999 | Le Mole . |

FOREIGN PATENT DOCUMENTS

| | | |
|---|---|---|
| 0 544 485 | 6/1993 | (EP) . |
| 95 17127 | 6/1995 | (WO) . |
| 58 52475 | 11/1998 | (WO) . |
| 98 52475 | 11/1998 | (WO) . |

* cited by examiner

Primary Examiner—Kevin Truong

(57) ABSTRACT

A site is prepared along a wall of a receiving blood vessel for connecting a prospective blood vessel thereto without interrupting the flow of blood through the receiving blood vessel. A device for the preparation comprises an elongated member and a sealing means. The device has a head portion to which the elongated member is connected, and a cutting means provided at a distal part of the head portion for making an initial opening in the receiving blood vessel. The sealing means is provided on the head portion proximally of the cutting means.

22 Claims, 11 Drawing Sheets

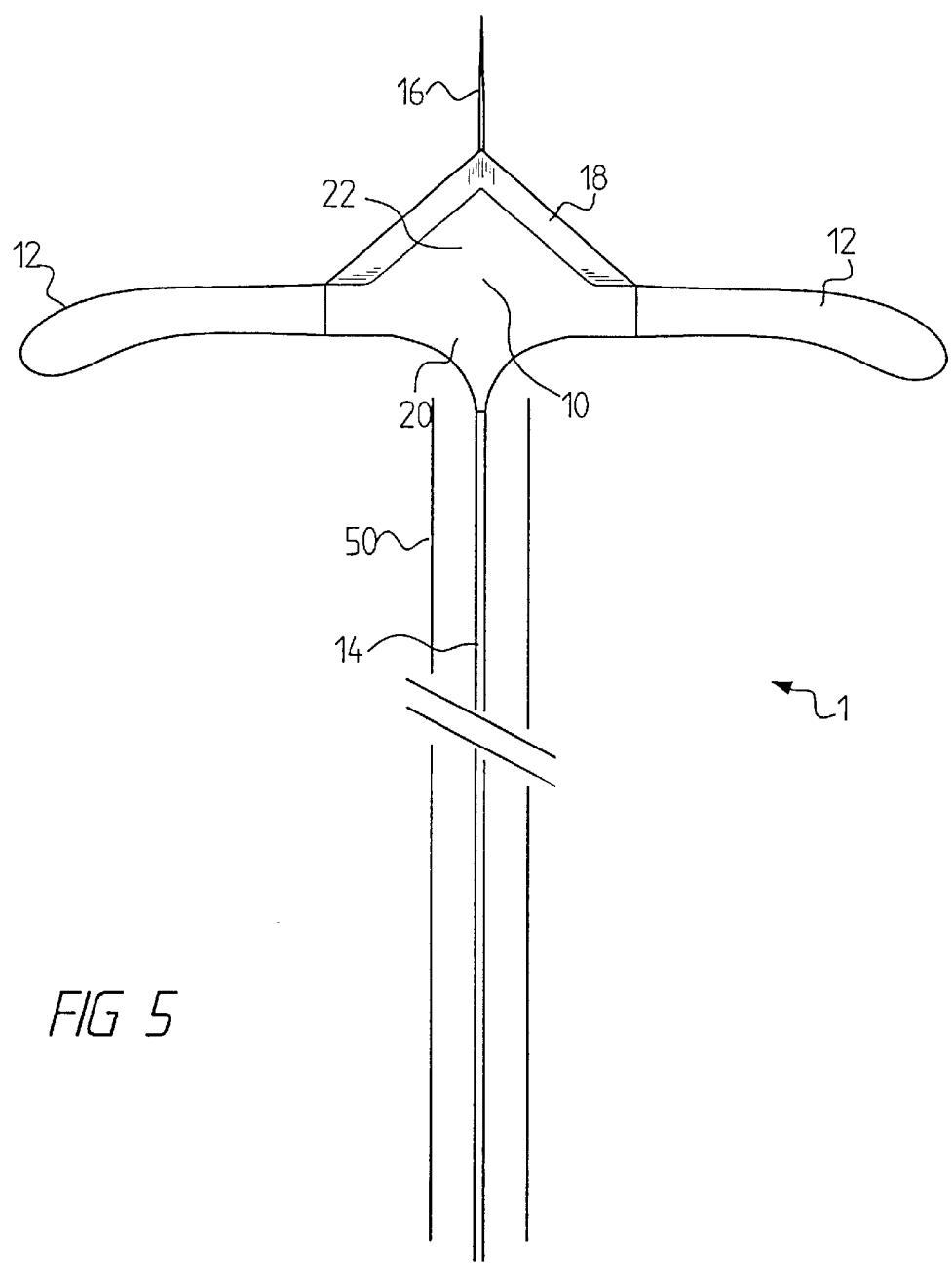

DEVICE AND METHOD FOR ENDOSCOPIC VASCULAR SURGERY

TECHNICAL FIELD OF THE INVENTION

The present invention relates to a device and a method for preparing a site along a wall of a receiving blood vessel for connecting a prospective blood vessel thereto without interrupting the flow of blood through the receiving blood vessel. The device comprises an elongated member and a sealing means.

BACKGROUND ART

Currently, the standard treatment of narrow and blocked arteries is to bypass the narrow part of the vessel with an additional vessel. When such an operation is to be performed the blood flow at the site where the additional vessel should be connected has to be excluded to prohibit bleeding. To exclude the blood flow, clamps normally are applied to the vessel which is to be connected to the additional vessel, either on one or both sides of the connection site. This can also be achieved by means of a side-clamp that excludes a part of the lumen around the intended opening.

Today, surgery is heading towards endoscopic surgery, also called keyhole surgery. To apply clamps on arteries through endoscopic ports is very demanding and sometimes impossible, especially on the aorta.

One way of reducing the problems described above is by using the device described in WO 98/52475. However, the preparation of a site for connecting a prospective blood vessel using this device is complicated and time-consuming. This results in the fact that the time for sealing is long and thus blood will be leaking out of the receiving blood vessel. Further, the device in WO 98/52475 is complicated because of its design, which makes it difficult to maintain, sterilize, and manufacture.

SUMMARY OF THE INVENTION

It is an object of the present invention to provide a device and a method for preparing a site along a wall of a receiving blood vessel for connecting a prospective blood vessel thereto without interrupting the flow of blood through the receiving blood vessel, and further to achieve this preparation by endoscopic surgery. Another object of the present invention is to provide a device and a method that will facilitate fast sealing of the receiving blood vessel for minimizing the amount of blood leaking out before the prospective blood vessel is connected.

These objects are achieved by a device according to claim 1 and by a method according to claim 14. Preferred embodiments of the present invention are defined in the dependent claims.

A device according to the invention comprises an elongated member and a sealing means and is characterized by a head portion to which the elongated member is connected, and a cutting means provided at a distal part of the head portion for making an initial opening in the receiving blood vessel, the sealing means being provided on the head portion proximally of the cutting means. An advantage of providing a cutting means and a sealing means like this is that the initial opening that is made by the cutting means may be sealed very fast by the sealing means, because both are arranged in the same device as mentioned above. The fast sealing of the initial opening results in a minimum of bleeding through this opening. Further advantages are that a hole for connecting a prospective blood vessel may be made without the use of clamps and thus very few instruments are required, which makes it easier to prepare said site.

In a preferred embodiment of the invention, a needle is provided on the head portion distally of the cutting means for penetrating the wall of the receiving blood vessel before the initial opening is made by the cutting means. By having the needle penetrate the wall of the receiving blood vessel at the site before any cutting or sealing is performed, the initial opening can be positioned with great accuracy. Further, the risk of the cutting means drifting away from a predestined position is minimized.

In another preferred embodiment of the invention, the cutting means comprises at least one cutting edge provided distally of the head portion. This facilitates the preparation of said site by making it possible for a user to both cut and seal during a single advancement of the device. Thus, the time between cutting an initial opening and sealing the same can be reduced to a very short time. Further, the head portion preferably tapers distally to facilitate the cutting of the initial opening and the advancement of the device through said opening.

In yet another preferred embodiment, the sealing means is a flexible disc extending radially outwards from the head portion in a relaxed state. As a result, the sealing means does not require any mechanical controlling means for sealing the opening in the blood vessel. In yet another preferred embodiment, the flexible disc is flexible in a way that makes it bend backwards along the elongated member as a result of the flexible disc making contact with the receiving blood vessel during the advancement of the head portion through the initial opening of the receiving blood vessel and makes the flexible disc resume its relaxed state when the disc has passed through the initial opening for sealing the initial opening from inside the receiving blood vessel. By designing the sealing means like this, the operation of cutting an initial opening and sealing it can be performed by involving very few and simple operations. It is even possible to perform the cutting and sealing by just advancing the device through the wall of a receiving blood vessel.

BRIEF DESCRIPTION OF THE DRAWINGS

The invention will now be described in more detail with reference to the accompanying drawings, in which FIG. 4 shows an introducer tube for guiding and initially operating the device according to the invention, FIG. 5 shows the device according to FIGS. 1 and 2 in combination with the introducer tube according to FIG. 4.

DETAILED DESCRIPTION OF PREFERRED EMBODIMENTS OF THE INVENTION

Figure 1:
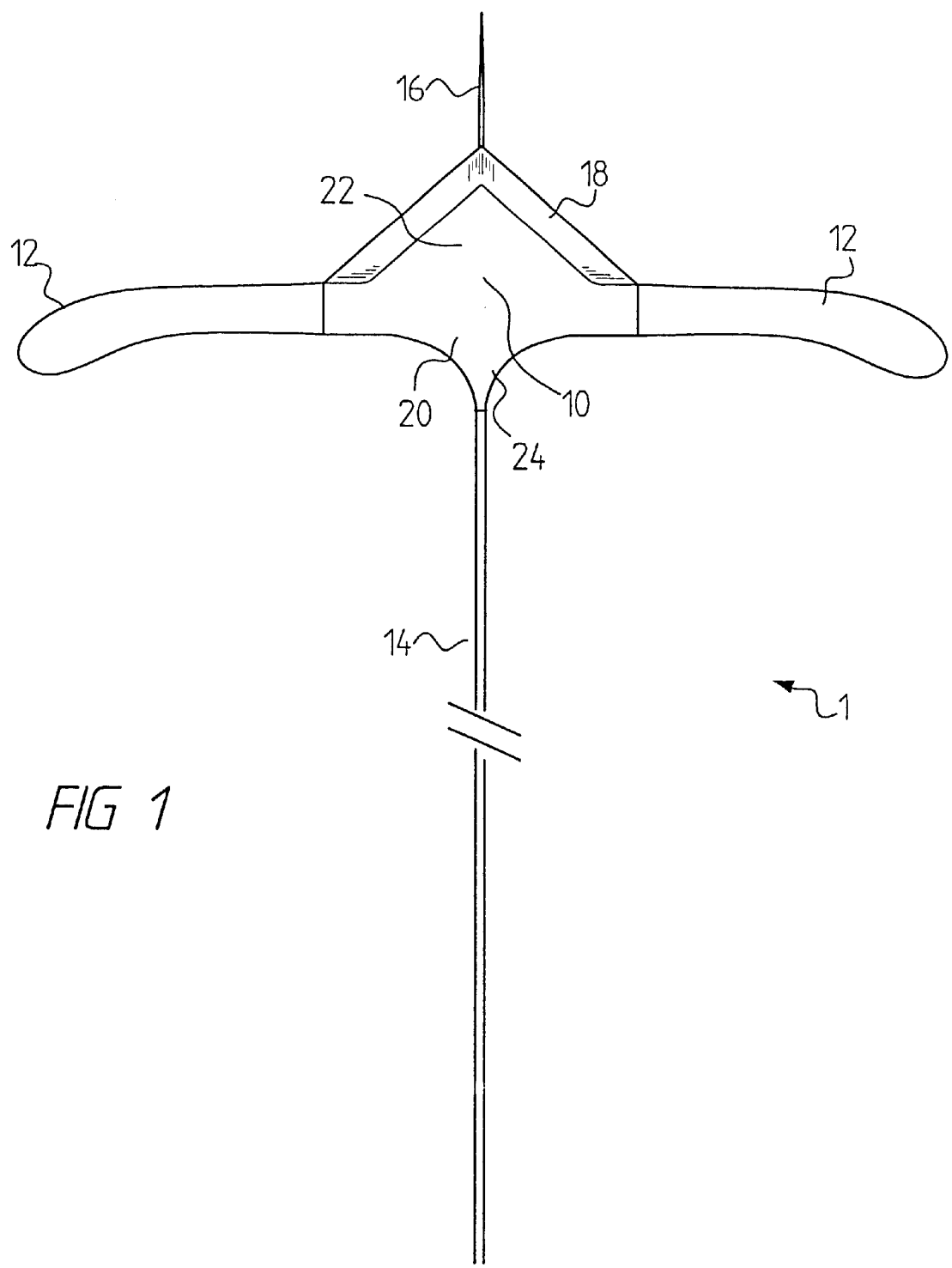
FIG. 1 shows a device according to one embodiment of the invention from the side.
Figure 2:
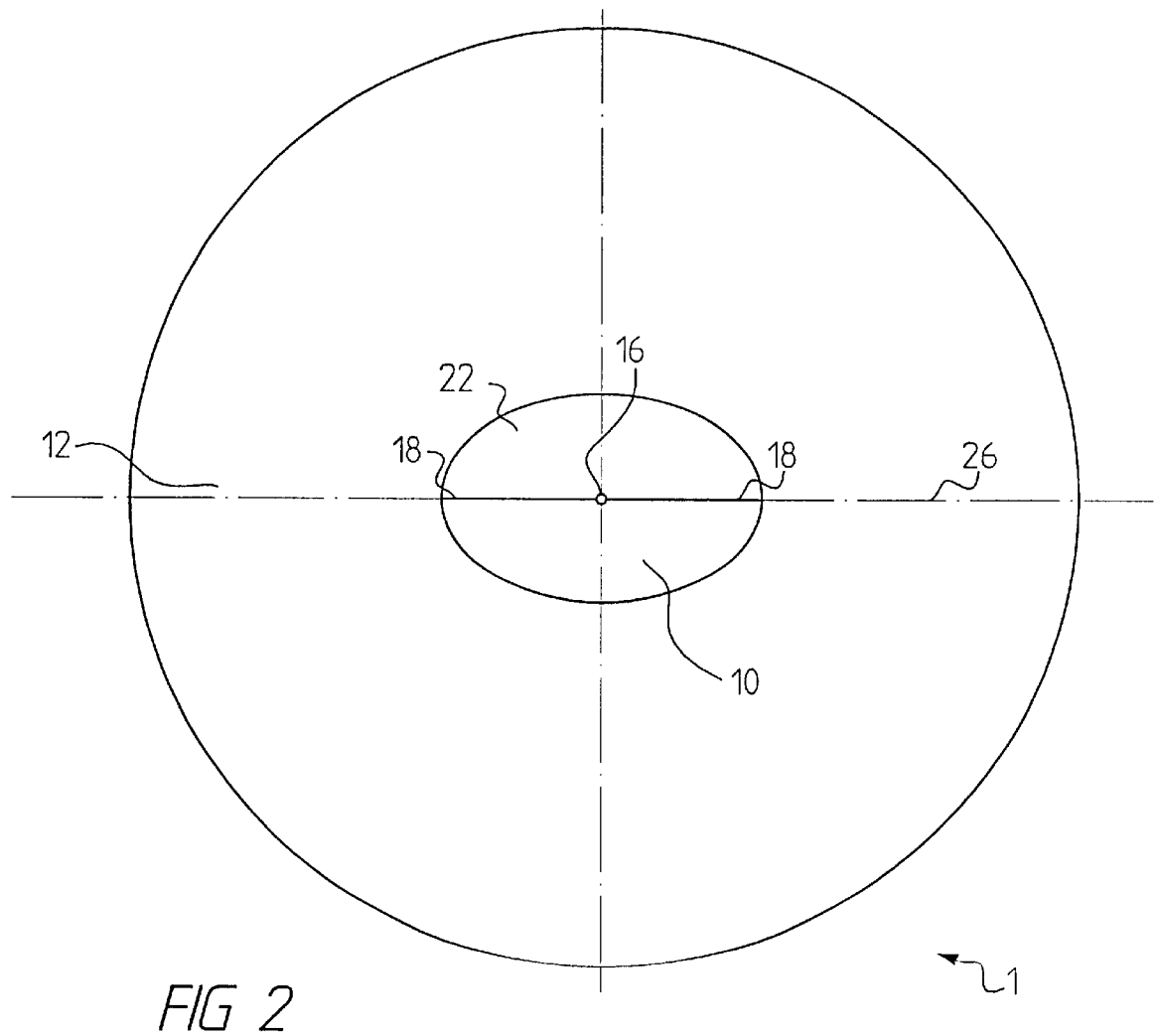
FIG. 2 shows the device according to FIG. 1 from its distal end.

FIGS. 1 and 2 illustrate a cutting and sealing device 1 according to a preferred embodiment. The device 1 essentially comprises a head portion 10, sealing means 12, and an elongated member 14. The sealing means 12 and the elongated member 14 are connected to the head portion 10.

The head portion 10 is preferably made of a hard material, e.g. metal or a hard synthetic material such as plastic, PVC, delrin, or any other synthetic material. Further, it is preferably oval in shape when viewed in a direction parallel to the direction of movement during use, see FIG. 2.

A distal part 22 of the head portion 10, in the preferred embodiment, tapers distally to facilitate the advancement of the head portion 10 through an initial opening in a receiving blood vessel at a site where a prospective blood vessel is to be connected.

At the distal part 22 of the head portion 10 there is provided a cutting means 18 for cutting the initial opening in the blood vessel. In the preferred embodiment, the cutting means 18 is a cutting edge arranged at the surface of the distally tapered distal part 22 of the head portion 10. The cutting edge is arranged along an axis 26 that is the longest central axis of the oval shape of the head portion 10. However, the cutting means 18 could be a cutting edge of any shape as long as it creates an initial opening during the advancement of the cutting means 18 through the wall of the blood vessel.

In the preferred embodiment, a needle 16 is arranged at the distal part 22 of the head portion 10 to facilitate and ensure that the penetration and the cutting is made at exactly the right position.

In a proximal part 20 of the head portion 10 a protrusion 24 is arranged for connecting the elongated member 14 to the head portion 10. Preferably, the protrusion 24 tapers proximally, and even more preferably it tapers proximally and has a concave surface.

The elongated member 14 is connected to the proximal part 20 of the head portion 10 for the purpose of keeping the device 1 in place when sealing the opening and withdrawing the device when it is not needed any more. The elongated member 14 may also be used to guide other equipment to the site. For example, equipment could be slidingly attached to the elongated member 14 and thus be transported along the elongated member 14 to the site. The elongated member may be a wire made of synthetic material, e.g. PTFE, polyethylene, PDS, etc, or a metal.

Figure 3A:
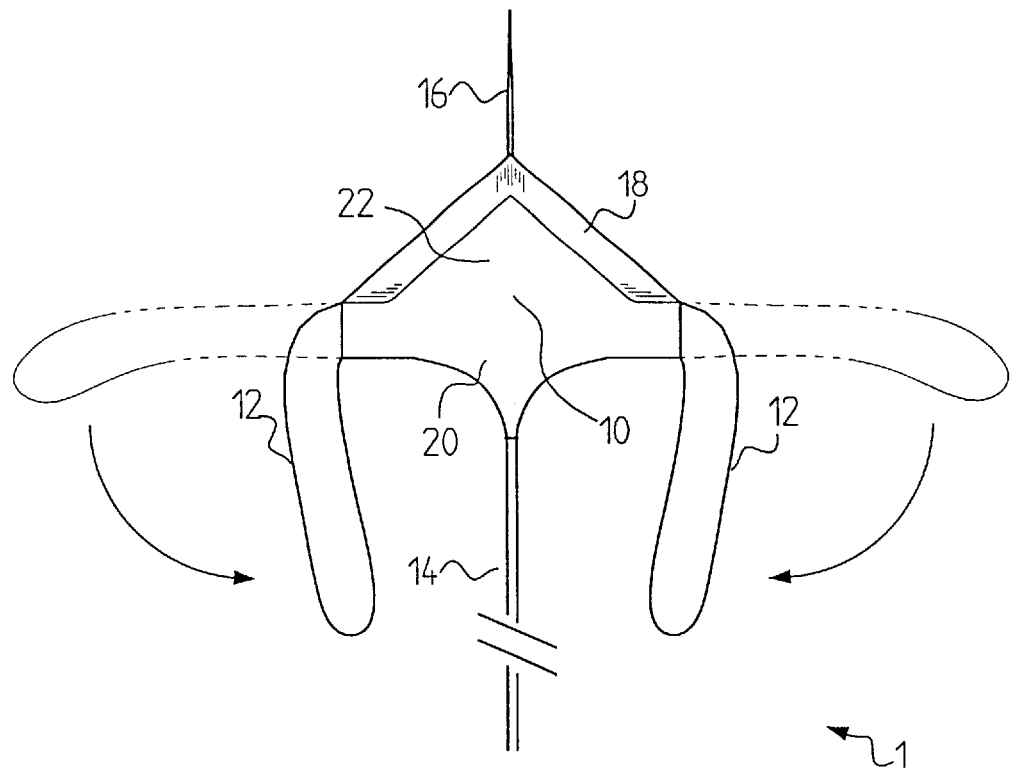
FIG. 3a shows the device according to FIGS. 1 and 2 when the sealing means is bent back during advancement through the wall of a receiving blood vessel.
Figure 3B:
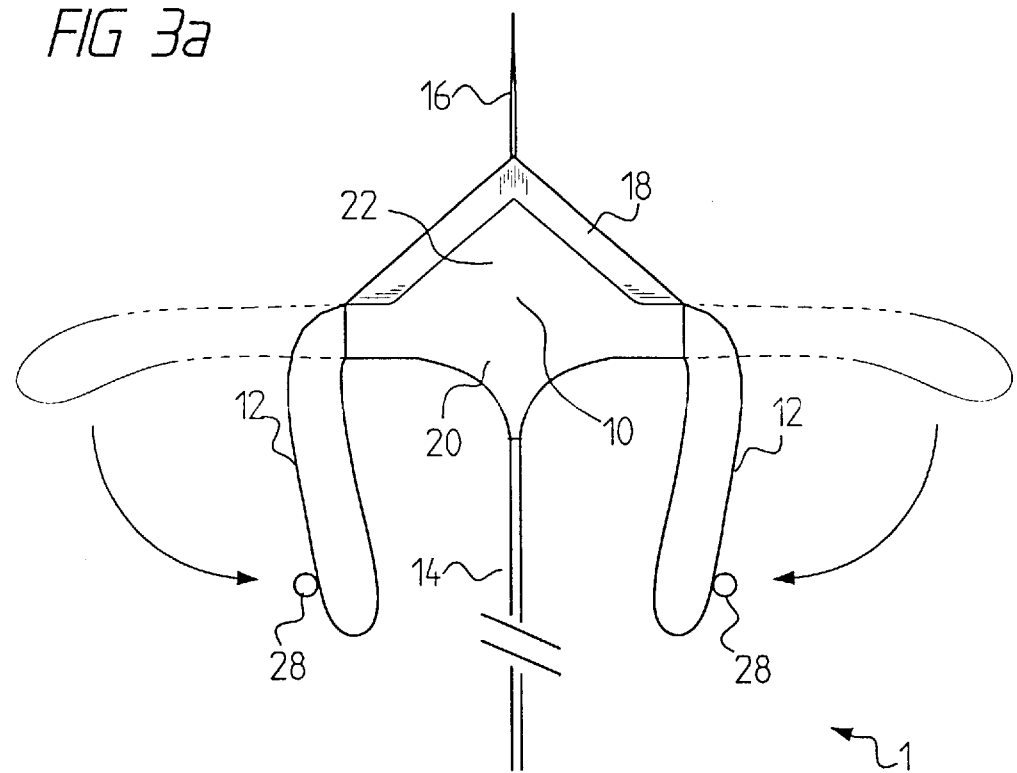
FIG. 3b shows the device according to FIGS. 1 and 2 when the sealing means is bent back by means of a ring.

The sealing means 12 is arranged on the head portion 10 for the purpose of sealing the opening in the receiving blood vessel from inside the blood vessel. Thus, bleeding through the opening is prevented. The sealing means 12 is preferably a soft, bendable, circular disc, and is for example made of a synthetic material such as polyethylene, polyurethane, PVC, silicone, or PTFE. The disc is so soft and bendable that it is able to bend back along the elongated member 14 during advancement through the initial opening in the receiving blood vessel, see FIG. 3a. On the other hand, the disk is so rigid that it will not be pushed out of the initial opening or an enlarged opening in the wall of the receiving blood vessel by the blood pressure. When the disc has passed the wall of the receiving blood vessel, it returns to its relaxed state for sealing the opening. Referring to FIGS. 3a and 3b, the disc is bent backwards during the penetration by forces from the edges of the initial opening, but optionally it can initially be fixed in the backwardly bent position by, for example, a synthetic ring 28 or a tape, which is released during the advancement of the disc through the initial opening.

Referring to FIG. 5, the device is shown together with an introducer tube 50, shown in FIG. 4, for guiding and initially controlling the device. The introducer tube 50 may be made of metal or any synthetic material. Further, it may be non-bendable, partially bendable or bendable in its full length, depending on the requirements of bending the tube in order to direct the head portion of the device 1 to the site. The tube 50 surrounds the elongated member 14 of the device and is smaller in diameter than the head portion 10 of the device 1. The smaller diameter of the introducer tube makes it possible to exert force on the head portion 10 and make it penetrate the receiving blood vessel.

Figure 12:
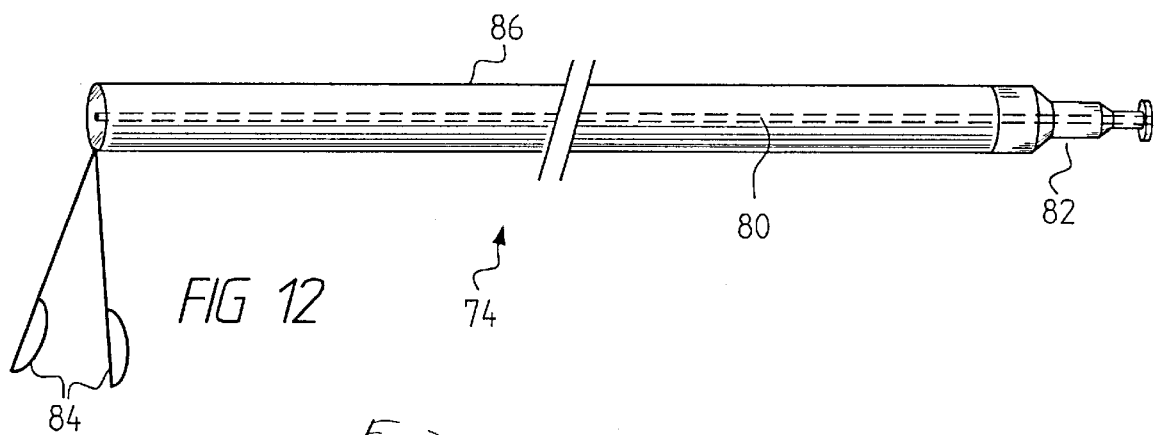
FIG. 12 shows a second cutting device.
Figure 13:
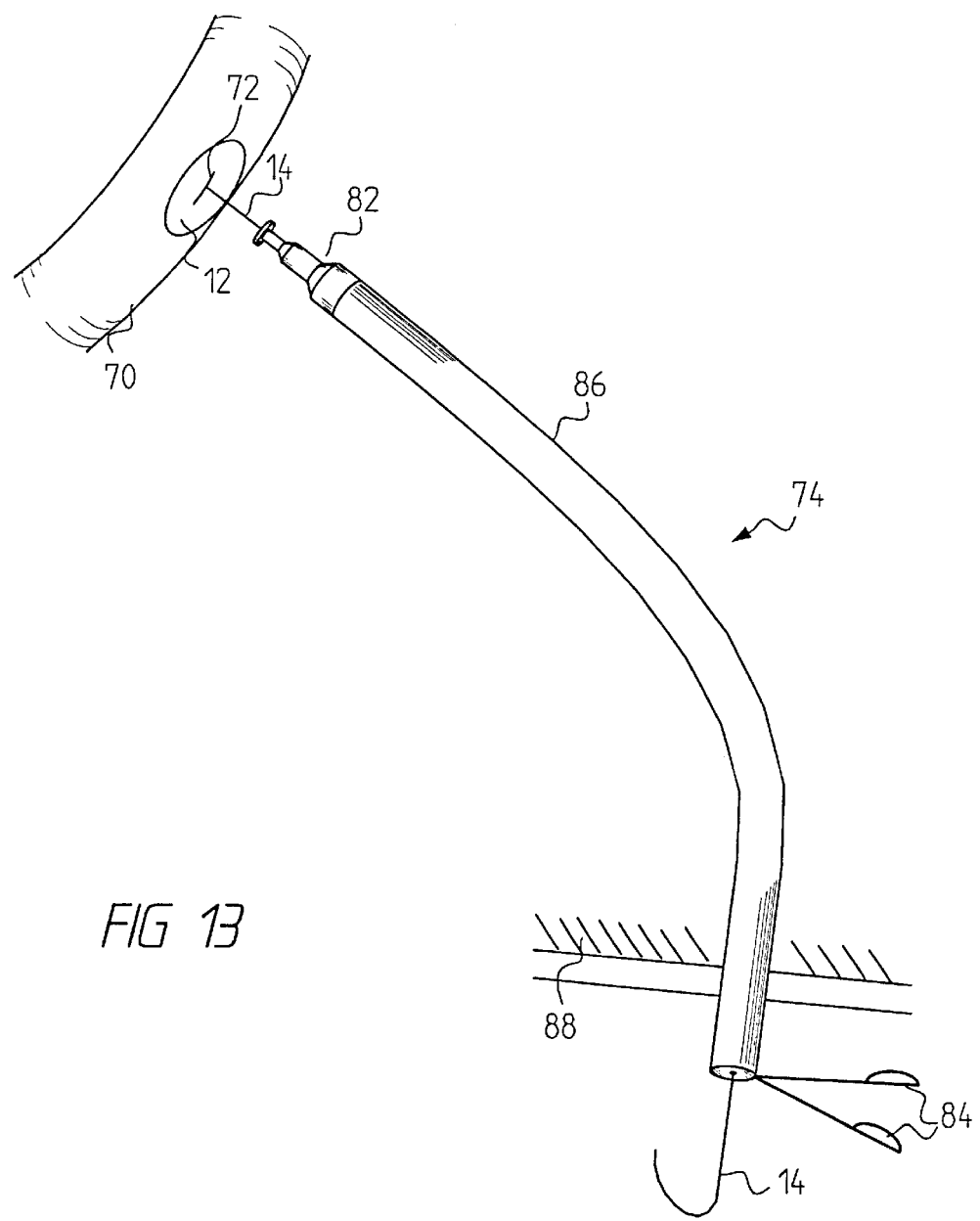
FIG. 13 shows the second cutting device of FIG. 12 when it is guided to the receiving blood vessel.

Referring to FIGS. 12 and 13, an embodiment of the present invention comprises a second cutting device 74, e.g. a punching device or a biting device. The cutting device 74 is preferably a punching device and is designed to be guided by the elongated member to the site where a hole is to be cut. In a preferred embodiment the punching device comprises a central channel 80, a punching mechanism 82 in a distal end of the punching device 74, maneuvering means 84 in a proximal end of the punching device 74, and an elongated body 86. The punching mechanism 82 is arranged to be controlled by the maneuvering means 84 from outside a body 88. Thus, a hole is punched inside the body 88 by means of the punching mechanism 82 by maneuvering the maneuvering means 84 being positioned outside the body 88. The maneuvering means 84 can be formed with a scissor-grip or just as two rods. To guide the punching device 74 to said site the central channel 80 is arranged for sliding the punching device 74 on the elongated member 14. The elongated body 86 is preferably a tube surrounding the central channel 80, which tube is flexible in order to follow bends of the elongated member 14.

Figure 6:
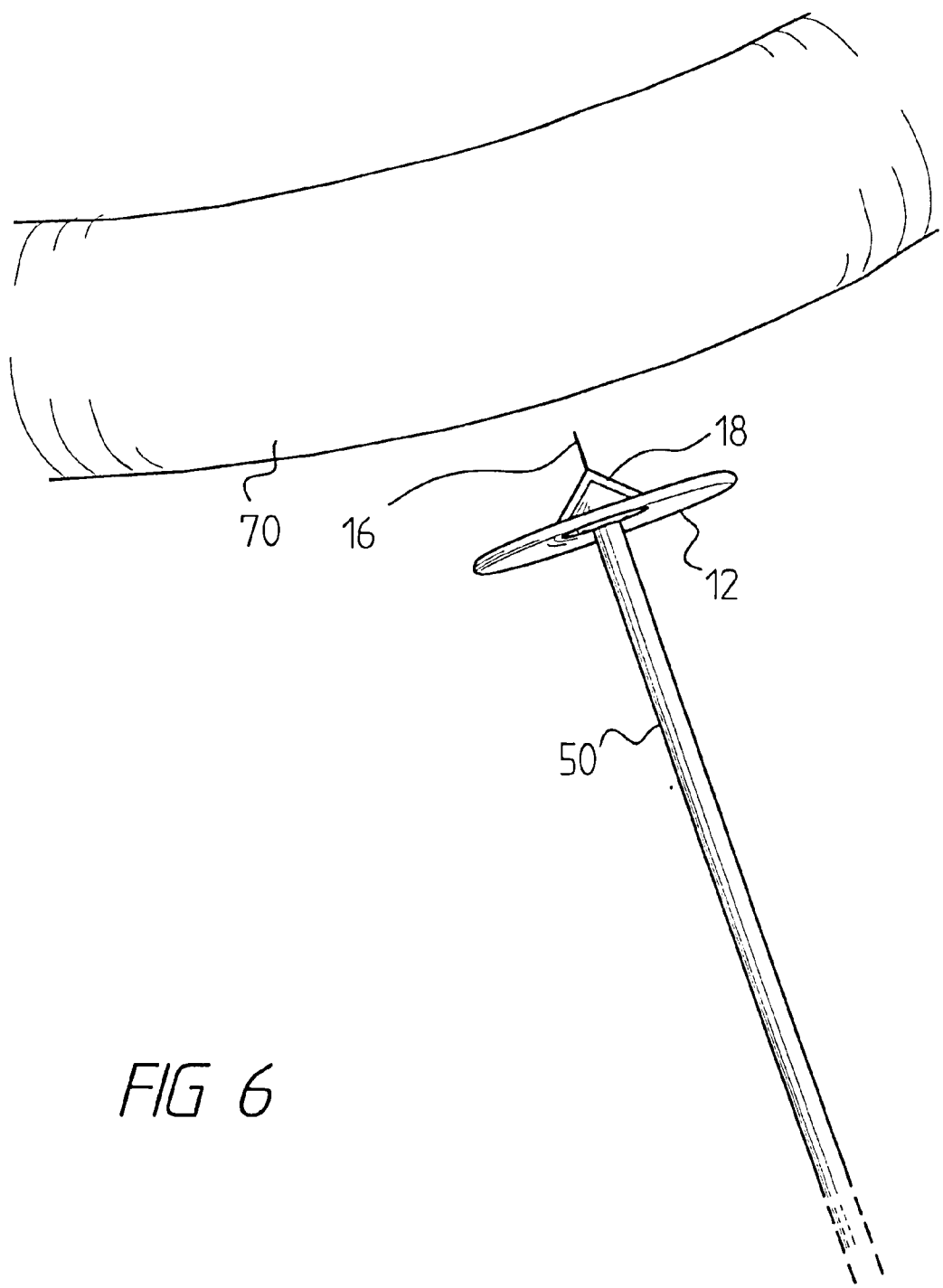
FIG. 6 shows the device according to FIGS. 1 and 2 being guided towards a receiving blood vessel.

Now referring to FIG. 6, in a preferred method according to the invention, the cutting and sealing device 1 is guided to the site of a receiving blood vessel 70, e.g. an artery, where a prospective blood vessel is to be connected. The means used for guiding and initial operation of the device 1 is preferably the introducer tube 50, but could be any other means that are able to guide and initially operate the device. The advantage of using an introducer tube is that it is a non-complex device, as explained.

Figure 7:
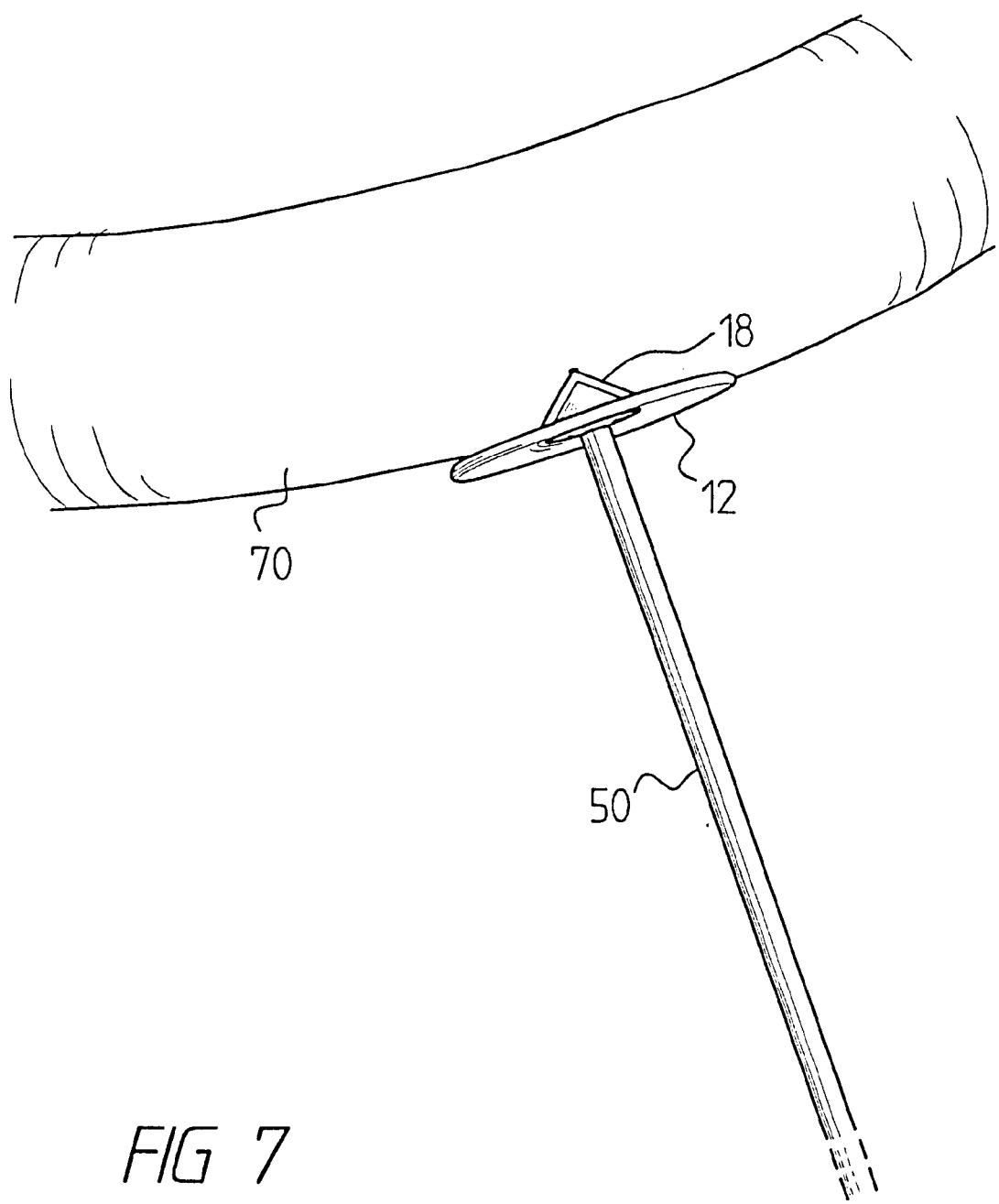
FIG. 7 shows the device according to FIGS. 1 and 2 having its needle penetrating the receiving blood vessel.

Now referring to FIG. 7, when the device 1 is positioned at the site, the needle 16 adjacent to the head portion 10 is easily directed to the exact location for the operation and pushed into the blood vessel 70 by means of the introducer tube 50.

Figure 8:
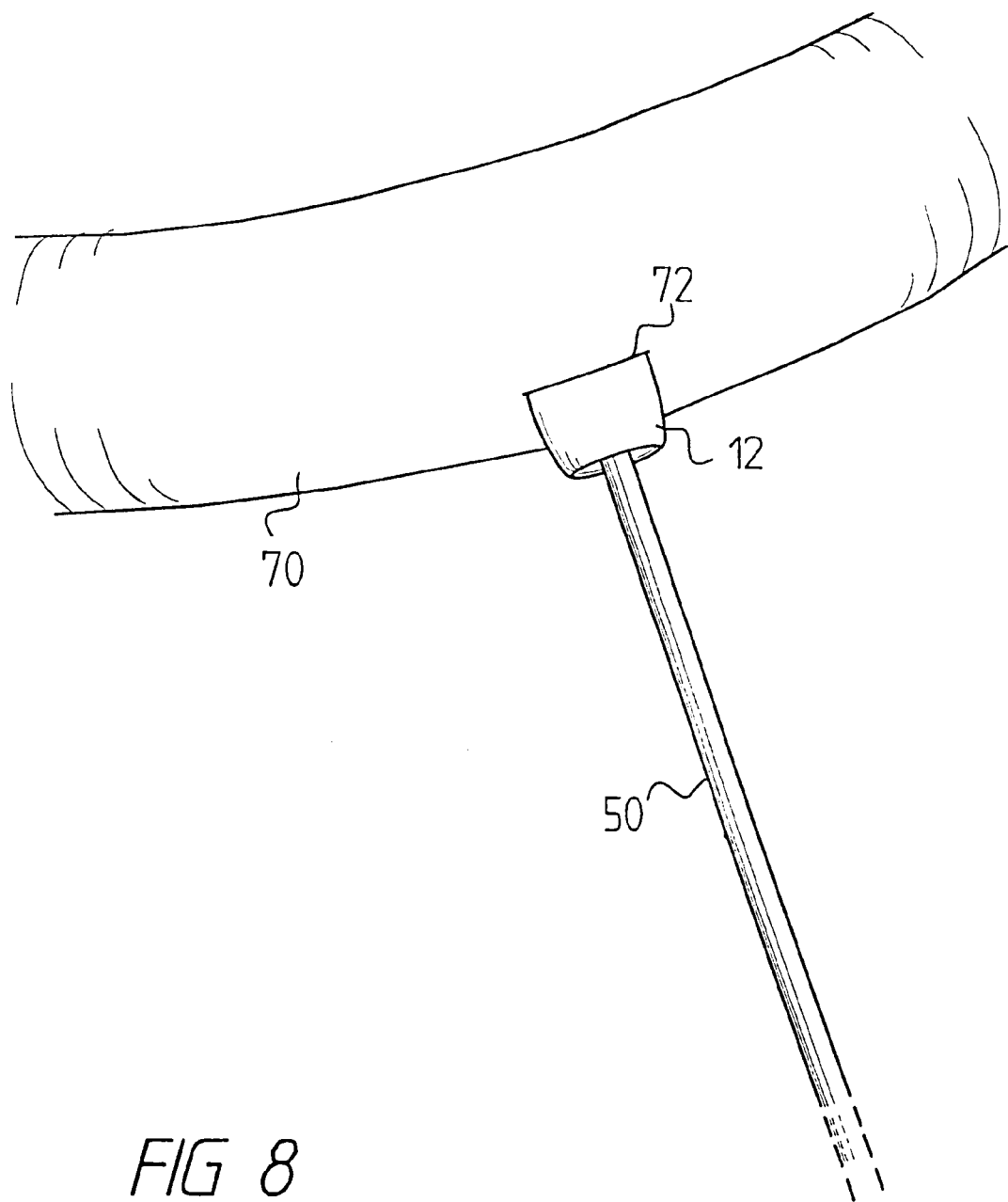
FIG. 8 shows the device according to FIGS. 1 and 2 passing through an initial opening made by the device.

Now referring to FIG. 8, the device 1 is further advanced so that the cutting means 18 is cutting an initial opening 72 in the wall of the receiving blood vessel 70 simultaneously as it is advanced through the same. The device 1 is further advanced and the sealing means 12 is bent back along the tube 50 by forces from the edges of the initial opening 72. The device is further advanced until the sealing means 12 has passed the wall of the receiving blood vessel 70 totally. Alternatively, the sealing means could initially be arranged in a backwardly bent position by means of a synthetic ring or a tape, which is released during the passage of the sealing means through the wall of the receiving blood vessel 70.

Figure 9:
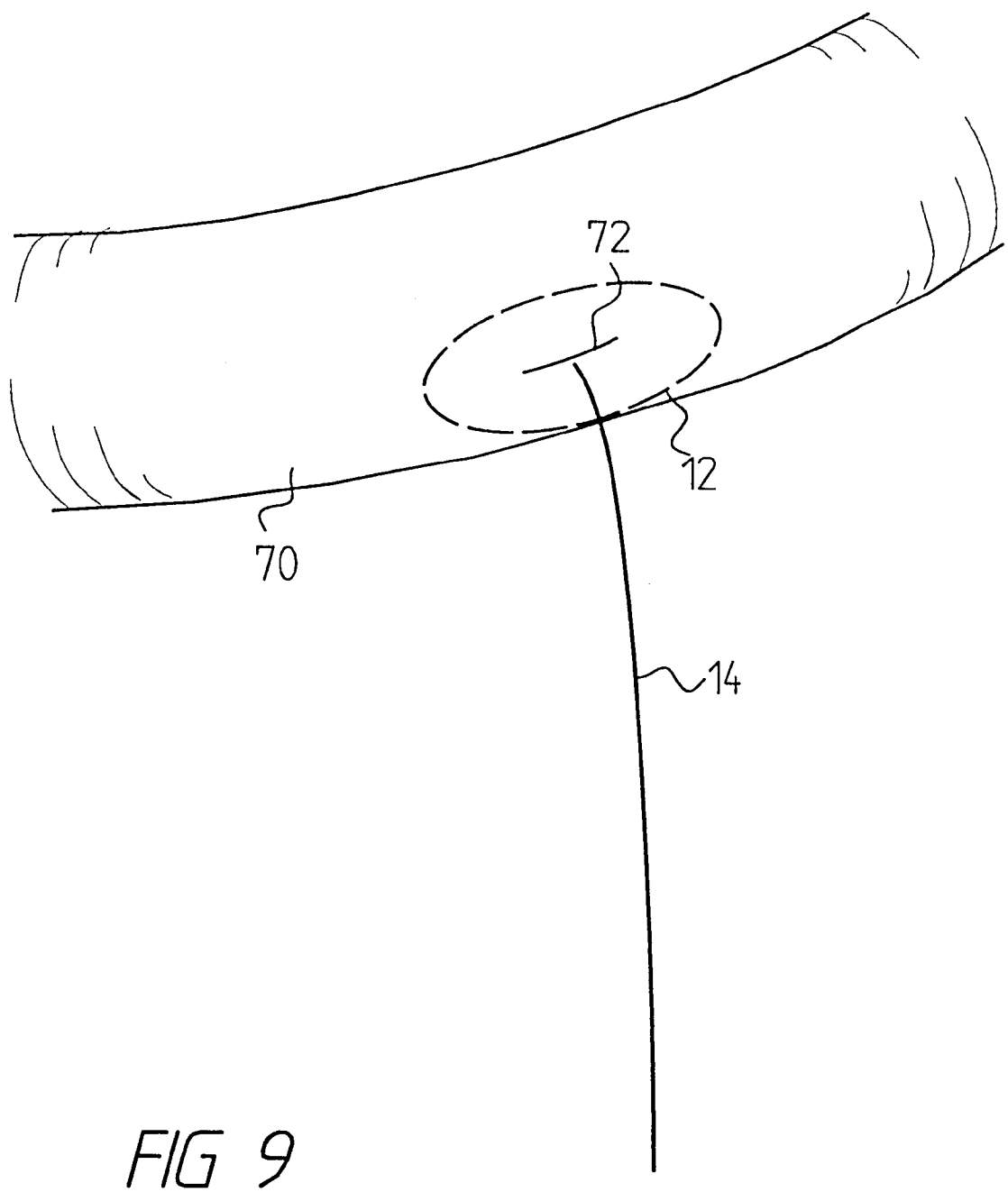
FIG. 9 shows the device according to FIGS. 1 and 2 sealing the initial opening from inside the receiving blood vessel.

Now referring to FIG. 9, when the sealing means 12 has passed the wall of the receiving blood vessel 70, it resumes its relaxed state and covers the initial opening 72. To ensure that the sealing means keeps its sealing position, a slight traction may be applied to the elongated member 14.

Figure 10:
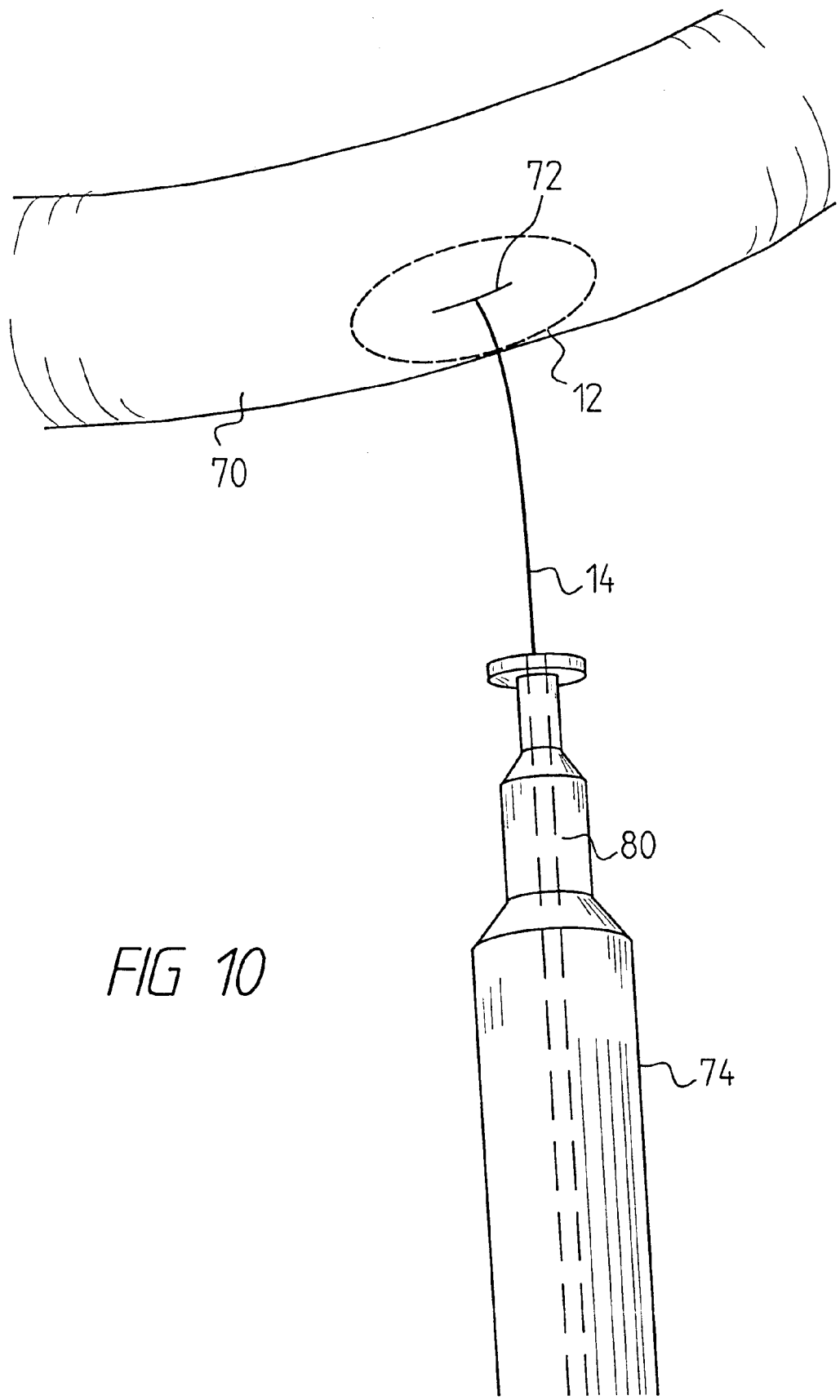
FIG. 10 shows a punching device being guided to the site by means of the elongated member of the device in FIGS. 1 and 2.
Figure 11:
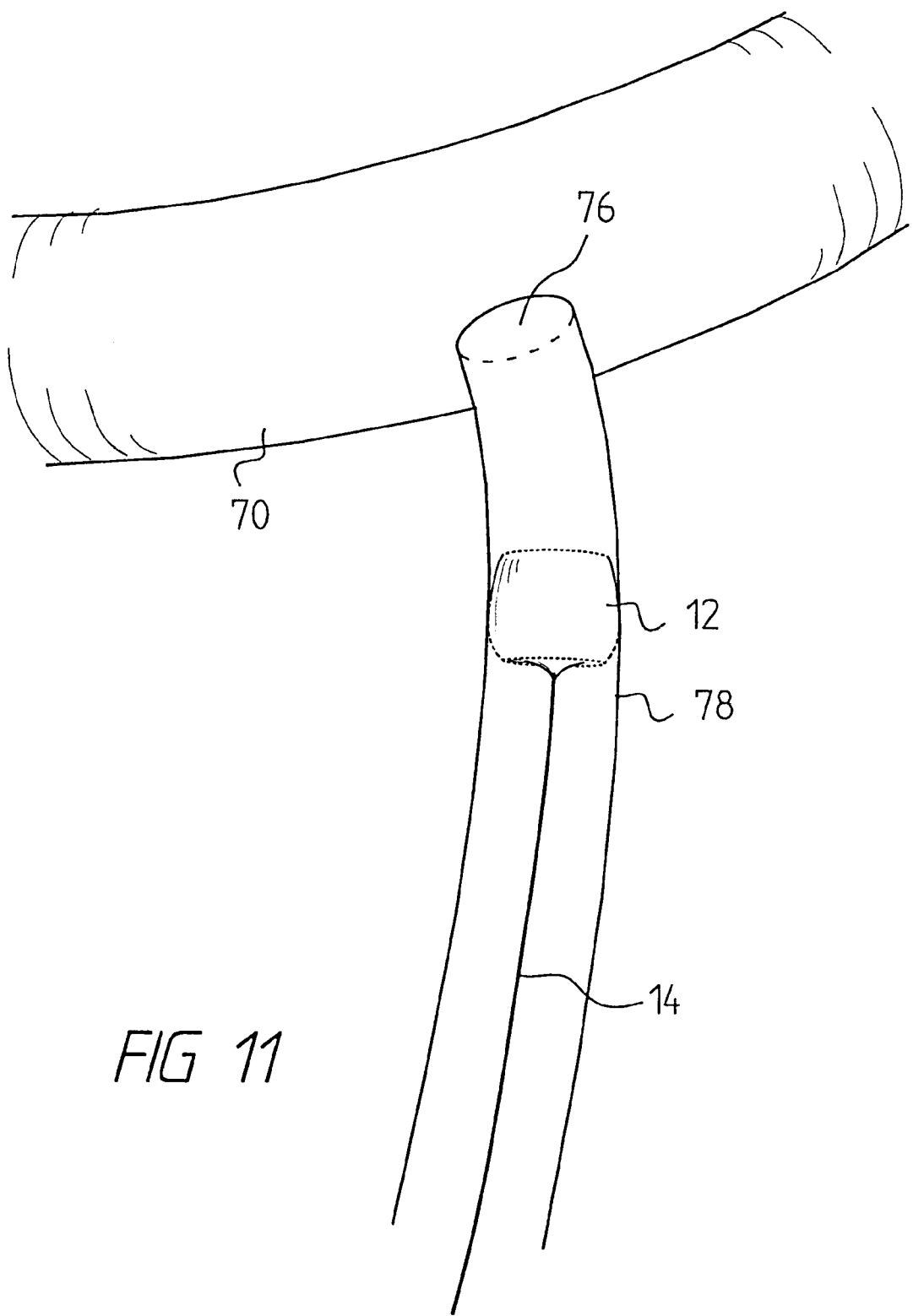
FIG. 11 shows a prospective blood vessel connected to the receiving blood vessel and shows the device according to FIGS. 1 and 2 having been retracted from its sealing position inside the receiving blood vessel through a newly created opening in the wall of the receiving blood vessel and then being retracted through the lumen of the newly connected prospective blood vessel.

Now referring to FIGS. 10 and 11, a second cutting device 74, e.g. a punching device or biting device, is arranged to be guided by the elongated member 14 to the site for cutting a final larger opening 76 in the wall of the receiving blood vessel. The elongated member 14 is preferably running through the second cutting device 74, which will thus be able to cut the final larger opening 76 at the location of the initial opening 72. When the second cutting device 74 is in position at the initial opening 72 it is operated to cut or punch a round hole, i.e. the final opening 76, in the receiving blood vessel 70.

The sealing means 12 is also sealing the final opening 76. When the final opening 76 is made, the second cutting device 74 is retracted and the material that has been removed by means of the second cutting device 74 is discarded when the second cutting device 74 is outside the body. Then the prospective blood vessel 78 is attached to the receiving blood vessel 70 at the final opening 76 by means of suturing or anastomotic devices. Finally, when the prospective blood vessel 78 is attached and the connection is sealed the cutting and sealing device 1 is retracted through this newly attached blood vessel 78.

What is claimed is:

1. A device for preparing a site along a wall of a receiving blood vessel for connecting a prospective blood vessel thereto without interrupting the flow of blood through the receiving blood vessel, said device comprising:
   an elongated member,
   a head portion to which the elongated member is connected,
   a cutting means provided at a distal part of the head portion for making an initial opening in the receiving blood vessel, and
   a sealing means configured for insertion into the blood vessel and provided on the head portion proximally of the cutting means, wherein the sealing means is a flexible disc extending radially outwardly from the head portion when in a relaxed state.

2. The device according to claim 1, wherein a needle is provided on the head portion distally of the cutting means for penetrating the wall of the receiving blood vessel before the initial opening is made by the cutting means.

3. The device according to claim 1, wherein the cutting means comprises at least one cutting edge provided distally of the head portion.

4. The device according to claim 1, wherein the head portion tapers distally.

5. The device according to claim 1, wherein a proximal part of the head portion comprises a protrusion to which the elongated member is attached, the protrusion tapering proximally.

6. The device according to claim 1, wherein the head portion is oval in shape when viewed along the direction of operational movement.

7. The device according to claim 1, wherein the elongated member is a wire.

8. The device according to claim 1, wherein the flexible disc is flexible in a way that makes it bend backwards along the elongated member as a result of the flexible disc making contact with the receiving blood vessel during the advancement of the head portion through the initial opening in the receiving blood vessel, the flexible disc resuming its relaxed state when the disc has passed through the initial opening for sealing the initial opening from inside the receiving blood vessel.

9. The device according to claim 1, further comprising a tube having the head portion at a distal end and enclosing the elongated member for guiding the head portion towards the receiving blood vessel.

10. The device according claim 1, further comprising a punching device having a central channel for sliding on the elongated member.

11. The device according to claim 6, wherein the punching device comprises a punching mechanism of cooperating cutting edges controlled by maneuvering means at proximal end of the punching device outside a body.

12. The device according to claim 6, wherein the punching device is flexible in order to follow bends when sliding on the elongated member.

13. A method for preparing a site along a wall of a receiving blood vessel for connecting a prospective blood vessel thereto without interrupting the flow of blood through the receiving blood vessel, the method comprising the steps of
   guiding a cutting and sealing device, comprising an elongated member, a sealing means, a head portion and a cutting means, to the site of the receiving blood vessel,
   cutting an initial opening in the wall of the receiving blood vessel by means of the cutting means of the device, and
   sealing the initial opening of the receiving blood vessel by advancing the sealing means of the device through the initial opening and making the sealing means seal the initial opening from the inside of the receiving blood vessel.

14. The method according to claim 13, further comprising, before the step of cutting, the step of penetrating the receiving blood vessel with a needle provided at a distal part of the head portion.

15. The method according to claim 13, wherein the cutting of the initial opening is performed by advancing the cutting means, which is provided with at least one cutting edge, through the wall of the receiving blood vessel.

16. The method according to claim 13, wherein a flexible disc is used as the sealing means.

17. The method according to claim 16, wherein the flexible disc, during the advancement in the sealing step, is bent backwards along the elongated member when advanced through the initial opening and wherein the flexible disc returns to a relaxed state when it has passed the wall of the receiving blood vessel completely.

18. The method according to claim 17 wherein the relaxed state of the flexible disc is a state in which the flexible disc extends radially outwardly from the head portion.

19. The method according to claim 13, wherein the cutting and sealing device is slightly retracted at the end of the sealing step to keep the sealing means positioned over the initial opening.

20. The method according to claim 13, wherein the cutting and sealing device is guided to the site of the receiving blood vessel by means of a tube.

21. The method according to 13, further comprising, after the step of sealing, the step of making a final opening) in the receiving blood vessel at the sealed site of the receiving blood vessel by means of a second cutting device.

22. The method according to claim 21, wherein the second cutting device is advanced to the site at the blood vessel along the elongated member.

* * * * *